United States Patent
Gila et al.

(10) Patent No.: US 7,502,116 B2
(45) Date of Patent: Mar. 10, 2009

(54) DENSITOMETERS AND METHODS FOR MEASURING OPTICAL DENSITY

(75) Inventors: Omer Gila, Cupertino, CA (US); William David Holland, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 814 days.

(21) Appl. No.: 10/658,939

(22) Filed: Sep. 9, 2003

(65) Prior Publication Data
US 2005/0052654 A1    Mar. 10, 2005

(51) Int. Cl.
*G01N 21/00* (2006.01)
(52) U.S. Cl. ........................................ 356/443
(58) Field of Classification Search .............. 356/443, 356/425, 445, 402, 406, 420, 446, 434, 448; 250/573, 574, 226, 214; 364/526, 525
See application file for complete search history.

(56) References Cited

U.S. PATENT DOCUMENTS

| | | | |
|---|---|---|---|
| 4,690,564 A | | 9/1987 | Morgenstern et al. |
| 4,750,838 A | * | 6/1988 | De Wolf et al. ............. 356/445 |
| 4,963,028 A | * | 10/1990 | Braun et al. ................. 356/445 |
| 5,053,822 A | | 10/1991 | Butler |
| 5,137,364 A | * | 8/1992 | McCarthy .................... 356/402 |
| 5,137,750 A | * | 8/1992 | Amin et al. .................. 427/116 |
| 5,204,538 A | * | 4/1993 | Genovese .............. 250/559.07 |
| 5,357,448 A | * | 10/1994 | Stanford ....................... 382/112 |
| 5,666,436 A | * | 9/1997 | Eames .......................... 382/167 |
| 5,854,680 A | * | 12/1998 | Rakitsch ..................... 356/406 |
| 5,864,353 A | | 1/1999 | Gila et al. |
| 6,028,674 A | | 2/2000 | Tognazzini |
| 6,229,972 B1 | | 5/2001 | Rushing |
| 6,384,918 B1 | * | 5/2002 | Hubble et al. ................ 356/402 |
| 6,462,821 B1 | * | 10/2002 | Borton et al. ................ 356/446 |
| 6,519,038 B1 | * | 2/2003 | Kritchman .................... 356/425 |
| 6,650,416 B2 | * | 11/2003 | Tandon et al. ................ 356/420 |
| 6,665,424 B1 | | 12/2003 | Stringa |
| 6,952,263 B2 | * | 10/2005 | Weiss et al. .................. 356/425 |
| 7,260,244 B2 | | 8/2007 | Shikami et al. |
| 2003/0007804 A1 | * | 1/2003 | Regelsberger et al. ......... 399/74 |
| 2003/0072002 A1 | | 4/2003 | Uejima |
| 2004/0057629 A1 | | 3/2004 | Shikami et al. |

(Continued)

FOREIGN PATENT DOCUMENTS

DE    1014071    9/2004

(Continued)

OTHER PUBLICATIONS

U.S. Appl. No. 11/250,784, filed Oct. 13, 2005; Gila et al.; "Imaging Methods, Imaging Device Calibration Methods, Imaging Devices, and Hard Imaging Device Sensor Assemblies"; having.

(Continued)

*Primary Examiner*—Roy M Punnoose
*Assistant Examiner*—Isiaka O Akanbi

(57) ABSTRACT

Methods for measuring optical density are described. The color on an area is determined. Based on the color, at least a first illumination source is selected. The area is illuminated with the selected illumination source. Radiation is received from the area, and the received radiation is converted to a signal indicative of optical density.

43 Claims, 5 Drawing Sheets

U.S. PATENT DOCUMENTS

| | | |
|---|---|---|
| 2004/0064213 A1 | 4/2004 | Vansteenkiste |
| 2005/0052654 A1 | 3/2005 | Gila et al. |
| 2006/0251320 A1 | 11/2006 | Diederichs et al. |

FOREIGN PATENT DOCUMENTS

| | | |
|---|---|---|
| DE | 10361936 | 7/2005 |
| EP | 1400922 | 3/2004 |
| GB | 2071573 | 9/1981 |
| WO | WO 2005094054 | 10/2005 |

OTHER PUBLICATIONS

"X-Rite: 504 Color Reflection Spectrodensitometer"; http://www.xrite.com/documents/literature/en/L7-169__504_en.pdf; 2004; 2 pp.

"X-Rite: 504 Color Reflection Spectrodensitometer"; http://www.xrite.com/documents/mktg/27-169.pdf.

* cited by examiner

DENSITOMETERS AND METHODS FOR MEASURING OPTICAL DENSITY

FIELD OF THE INVENTION

The invention generally relates to densitometers and methods for measuring optical density.

BACKGROUND OF THE INVENTION

Densitometers are used to control color in a printed product. Color control is desirable so that a color printed with a printing apparatus matches, for example, the same color displayed on a monitor, or generated by a scanner, camera, or other device, or printed by another apparatus. Color consistency is desirable across consecutive pages of a multi-page printed document, job to job, within the same page, and machine to machine.

Densitometers measure optical density, which is generally proportional to ink thickness. Briefly, a densitometer illuminates an area with light from an optical device and detects the light reflected or transmitted from the area. The reflected light is converted to an electrical signal, for example by a photodetector, and the resultant electrical signal is indicative of the ink thickness.

Printing apparatuses typically employ between 4 and 7 inks. Densitometers accordingly may include a light source and a plurality of filters or a plurality of light sources—each to illuminate, and determine the thickness of, a different ink color. For example, in one known system including a densitometer with a plurality of sequentially drivable light-emitting diodes (LEDs), the LEDs sequentially illuminate a measuring point and the reflected light is processed to determine ink density values. That is, light is received from illumination by each LED, one after another. The need to sequentially illuminate each desired area with a plurality of light sources limits the speed with which several areas can be measured.

Standards have been developed for defining the color spectrum—such as the ANSI T standard. Standards are typically based on illuminating an area with a light source having a particular spectrum, so that the reflected light can be universally interpreted. Accordingly, interference filters are used in one system to match the spectral intensities of the illuminating LEDs to spectral ranges provided for obtaining ink density values. The interference filters add complexity, expense to the system and reduce its reliability.

Further, some state of the art densitometers employ one or more incandescent Tungsten lamps. Generally, the Tungsten lamps add additional cost to the densitometer, and produce excess heat. The excess heat effects the densitometer reading and diminishes the accuracy of a densitometer employing a Tungsten lamp. Tungsten lamps take a certain amount of time to stabilize, which increases the time necessary to take a densitometer reading. The performance of a Tungsten lamp also changes over its lifetime, and aging effects can pose problems for the accuracy of the readings.

SUMMARY OF THE INVENTION

According to a first aspect of the present invention, methods for measuring optical density are described. The color printed on an area is determined. Based on the determined color, at least a first illumination source is selected. The area is illuminated with the selected illumination source. Radiation is received from the area, and the received radiation is converted to a signal indicative of optical density. In some embodiments, the signal indicative of optical density is a standardized signal indicative of standardized optical density. Further embodiments provide compensation for the effects of heating of the selected illumination source during illumination of the area. Heating compensation is provided in some embodiments by generating a corrected signal indicative of optical density using a non-linear relationship between the voltage across a light emitting diode and the signal indicative of optical density.

According to another aspect of the present invention, methods for calibrating a printing apparatus are provided. An area having a color is printed. Based on the printed color, at least one illumination source in a densitometer is selected. A signal indicative of optical density in the area is provided by the densitometer. In some embodiments a plurality of areas are printed each having a color. A signal indicative of optical density in each of the areas is then provided by the densitometer.

According to another aspect of the present invention, a densitometer is provided. Embodiments of the densitometer include first illumination source to illuminate an area. A sensor for receiving radiation from the area is provided. A processor is coupled to the sensor for converting the received radiation to a standardized signal indicative of standardized optical density.

In some embodiments, the processor is further configured to compensate for the effects of heating of the illumination source during illumination.

According to another aspect of the present invention, a printing apparatus is provided. Means for printing at least one ink on an area is coupled to a controller. A densitometer is further coupled to the controller, the densitometer positioned to illuminate the area and generate a standardized signal indicative of standardized optical density of the area.

According to another aspect of the present invention, a document or other article printed using embodiments of densitometers, methods, or printing apparatuses of the invention are provided.

BRIEF DESCRIPTION OF THE DRAWINGS

The present invention may be better understood, and its features and advantages made apparent to those skilled in the art by referencing the accompanying drawings.

DETAILED DESCRIPTION

Figure 1:
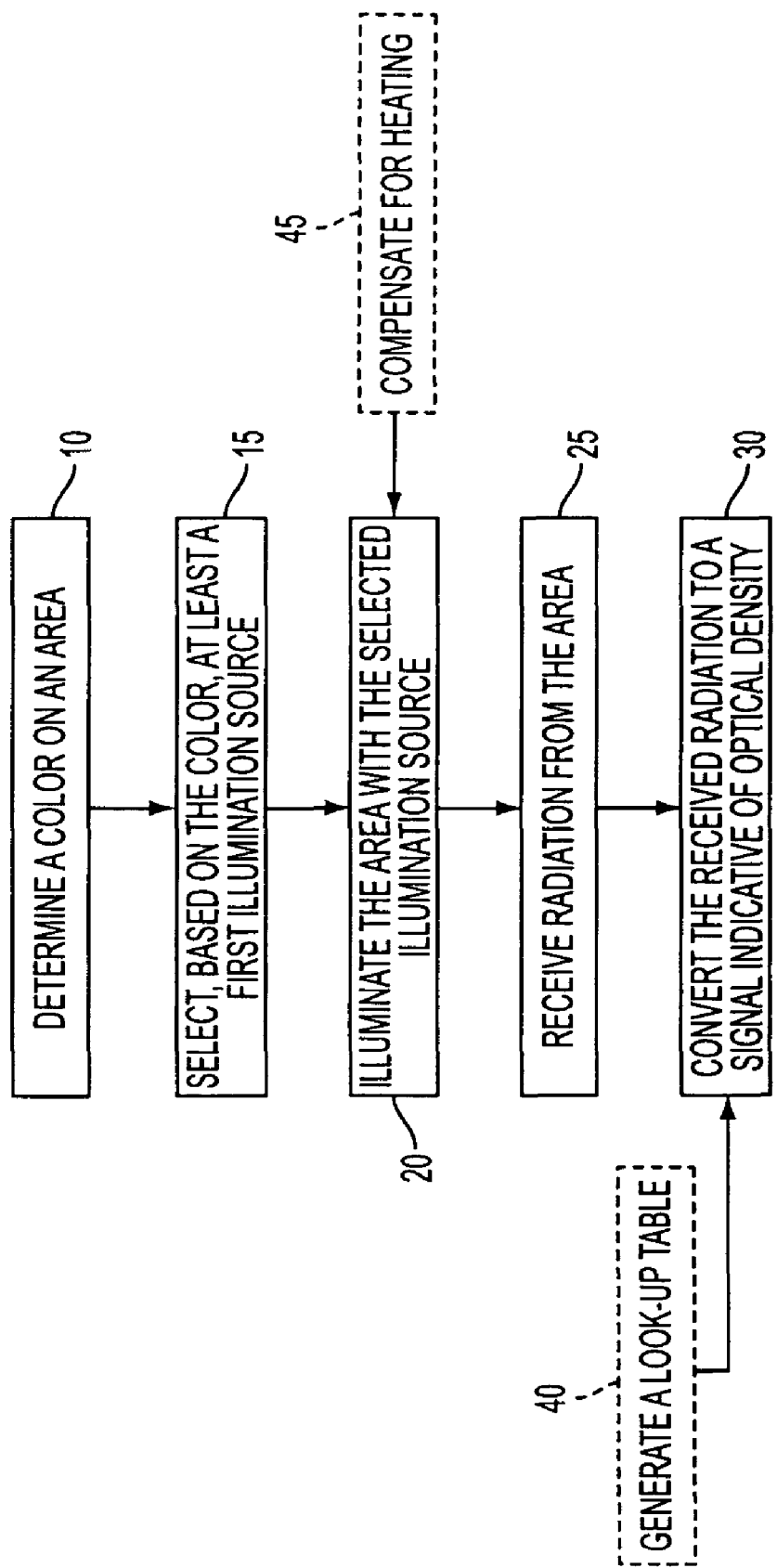
FIG. 1 depicts a method for measuring optical density, according to an embodiment of the present invention.

One embodiment of a method for measuring optical density according to the present invention is shown in FIG. 1. A color on an area is determined in step 10. For example, in accordance with embodiments of the invention, data is received that indicates the ink used to print an area. In typical printing apparatuses, any number of inks, including 1, 2, 3, 4, 5, 6, and 7 inks, or a greater number of inks are used. In accordance with embodiments of the present invention, cyan, magenta, yellow, and black inks are used in a printing apparatus. In some embodiments, additional inks are provided. The determination in step 10 indicates which ink, or combination of inks, in some embodiments, were used to print an area whose optical density will be measured. Accordingly, in some embodiments, data regarding inks used to print one or more areas are stored in a densitometer. The densitometer accesses the stored data to determine the color printed on an area. In other embodiments, data regarding one or more inks used to print an area are transmitted to the densitometer. In embodiments where a digital press is used, for example, information regarding the color being printed is available from the digital press itself. Accordingly, in some embodiments, the densitometer receives data similar to that stored in the digital press regarding colors to be printed. In some embodiments, the printing apparatus may transmit data regarding a color being printed to the densitometer.

Still referring to FIG. 1, based on the determined color, at least a first illumination source is selected in step 15. In some embodiments of the invention, the selected illumination source is a light-emitting diode. In some embodiments, the selected illumination source includes a plurality of light-emitting diodes. In some embodiments, the selected illumination source is a Tungsten lamp or other source of electromagnetic illumination. The selected illumination source may be chosen based, at least in part, on the color printed in the area, as indicated by the color determined in step 10. In accordance with embodiments of the invention, the illumination source is chosen from a group of available illumination sources, each having a different electromagnetic spectrum, typically red, green, and blue. The selected illumination source, in accordance with embodiments of the invention, will have an electromagnetic spectrum suitable for measuring the optical density of an area having the color indicated by the color determined in step 10. In some embodiments, an illumination source having a spectrum complementary to the color measured may be used. Typical complementary color pairs include Red-Cyan, Blue-Yellow, and Green-Magenta. Accordingly, in embodiments of the present invention, a red or orange light-emitting diode is selected to illuminate an area printed with Cyan ink, a green light-emitting diode is selected to illuminate an area printed with Magenta ink, a blue light-emitting diode is selected to illuminate an area printed with Yellow ink. In some embodiments, a fourth light source is included to facilitate pattern recognition or to compensate for ambient and/or internal reflections.

The area is then illuminated with the selected illumination source, in step 20 of FIG. 1. The illumination may occur, in accordance with embodiments of the invention, at any of a variety of distances and angles from the area. The distance and angle of illumination will be influenced by a variety of factors including, but not limited to, printing media, printing apparatus, illumination intensity, illumination source, resultant illumination spot size, lenses, and the method of receiving radiation from the area used. The invention is not restricted to any particular angle or distance as it is known how optics may be used to illuminate and collect radiation from surfaces at a variety of angles and distances and such optical systems may be used in conjunction with the densitometers, apparatuses, and methods described herein.

Radiation is then received from the area, in step 25, shown in FIG. 1. As described further below, in some embodiments radiation transmitted from the surface of the area is received. In some embodiments, radiation transmitted through the area is received. In some embodiments, both reflected and transmitted radiation are received, for example, if a gloss meter is used.

The received radiation is converted to a signal indicative of optical density in step 30, still referring to FIG. 1. For example, in one embodiment, the received radiation is collected by a light-to-voltage (LTV) sensor and converted to a voltage signal. The voltage signal generated is interpreted as an optical density as known in the art. In some embodiments, a plurality of readings are taken for an area, and the signals averaged to generate an average signal indicative of optical density. Other embodiments use one or more different statistical methods, instead or in addition to averaging, to generate a signal indicative of optical density. In one embodiment, optical density (OD) is calculated according to the equation:

$$OD = a \log(V_{ltv}) + b \tag{1}$$

where a represents slope, b represents an offset, and $V_{ltv}$ is the voltage generated by a light-to-voltage sensor. Generally, a and b are empirically determined values. Compensation for scattering and ambient light may also be employed, as known in the art.

Figure 2:
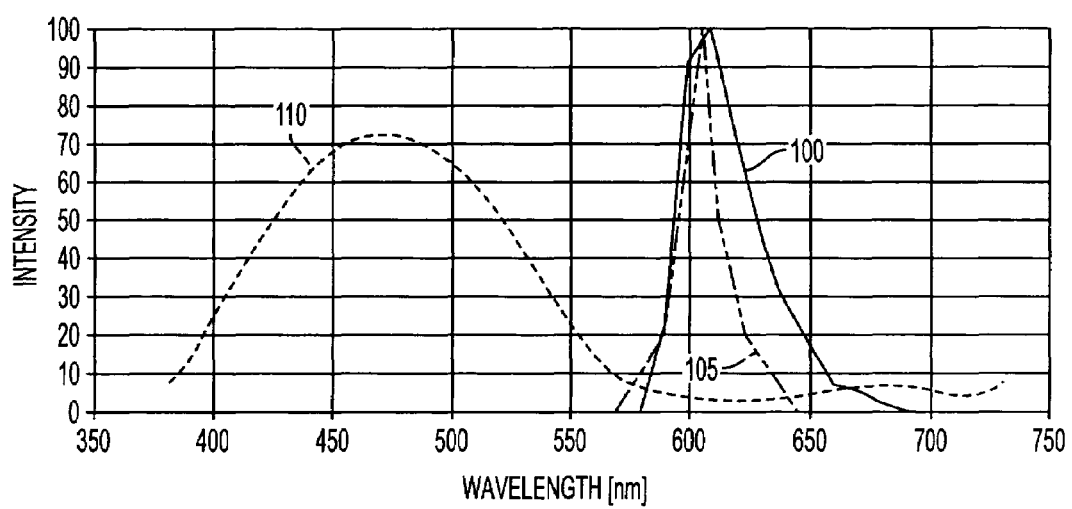
FIG. 2 depicts an illumination source spectrum, a standard spectrum, and an ink spectrum, each showing intensity versus wavelength according to an embodiment of the present invention.

In some embodiments, the received radiation is converted to a standardized signal indicative of standardized optical density, in step 30 of FIG. 1. Converting the received radiation to a standardized signal generally refers to compensating for the spectrum of illuminating radiation to the area measured. For example, in one embodiment, an area is illuminated with electromagnetic radiation having a first spectrum and the standardized signal generated represents a signal that would have been received during illumination of the area with electromagnetic radiation having a standard spectrum. This is advantageous, for example, when a standard measurement is desirable, such as an ANSI T-status, or other ANSI status measurement, such as, but not limited to, ANSI A status. Standards, such as the ANSI T-status, generally specify the spectrum of electromagnetic radiation used to illuminate an area and interpret the resultant signals. In some embodiments of the present invention, illumination sources are used that do not emit the spectrum of electromagnetic radiation specified by the standard. For example, FIG. 2 depicts a standard Red spectrum 100 as defined by the ANSI T-status standard to measure Cyan ink as well as a spectrum 105 of an orange LED used in one embodiment to measure Cyan ink, a spectrum 110 of which is also shown in FIG. 2. Each spectrum generally represents a plot of intensity versus wavelength. In accordance with embodiments of the present invention, ANSI T-status compliant measurements are obtained by converting the received radiation to a standardized signal indicative of standardized optical density. Accordingly, in one embodiment, the standardized signal is an ANSI T-status signal. So, for example, with reference to FIG. 2, a signal indicative of the optical density of an area printed with cyan ink is received after illumination with an orange LED having the spectrum 105. The signal is converted to a standardized signal indicative of the standardized optical density of the area generally representing a signal that would have been generated by illumination with the defined T-status red spectrum 100. In other embodiments, a different spectrum is used.

In accordance with embodiments of the invention, one or more look-up tables are generated for converting the received radiation to a standardized signal indicative of standardized optical density, in step 40, referring to FIG. 1. In some embodiments, the look-up table is provided. In other embodiments, one or more look-up tables are generated through one or more calibration measurements. To calibrate the densitometer used to measure optical density according to embodiments of the present invention, an area is printed with a color at a known density, and illuminated with a first illumination source chosen based on the printed color. In some embodiments, a plurality of calibration measurements are taken to generate a look-up table, while in some embodiments only one measurement is made. Values not explicitly in the look-up table may be interpolated from other values in the table, according to embodiments of the invention. In some embodiments of the invention, one look-up table is generated for each color to be measured. Accordingly, to convert received radiation to a standardized signal indicative of standardized optical density in step 30 of FIG. 1, in embodiments of the invention, an appropriate look-up table is selected based on the color of the area to be measured. The selected look-up table is used to associate the received radiation with a standardized signal indicative of standardized optical density.

Embodiments of methods according to the present invention include compensating for the effects of heating of the selected illumination source during illumination of the area, step 45 in FIG. 1. In some embodiments of the present invention, the signal indicative of optical density generated is effected by heating of the illumination source. Without being bound by theory, as the illumination source heats up, its intensity falls. In accordance with embodiments of the present invention, a corrected signal is calculated from the signal indicative of optical density. The corrected signal is calculated using a non-linear formula relating the signal to a control parameter of the illumination source. For example, in one embodiment the illumination source is a light-emitting diode and the sensor receiving radiation from the illuminated area is a light-to-voltage sensor. The voltage across the light-emitting diode is measured and the light-to-voltage (LTV) sensor value is modified as follows:

$$LTV_{corrected} = \frac{LTV}{1 - C\frac{V_{0\_LED} - V_{LED}}{V_{0\_LED}}} \quad (2)$$

Where LTV is the measured light-to-voltage sensor voltage, $LTV_{corrected}$ is the corrected sensor voltage, C is an empirical factor chosen depending on the LED color, current, and/or batch, $V_{0\_LED}$ is a baseline voltage and $V_{LED}$ is the operational voltage, or present voltage reading. This generally provides a non-linear relationship between the LED voltage and the light-to-voltage sensor voltage.

Figure 3:
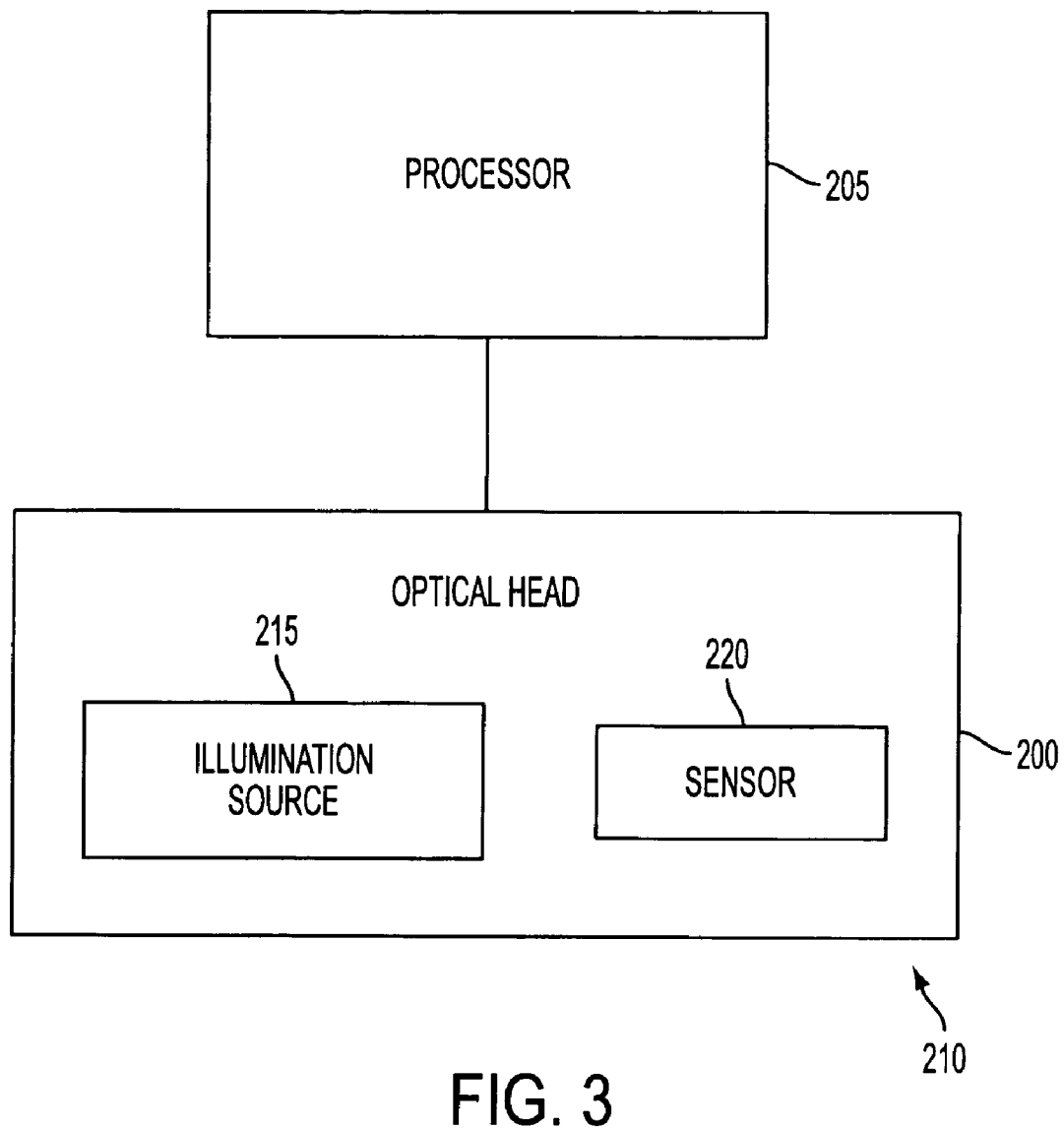
FIG. 3 depicts a densitometer, according to an embodiment of the present invention.

Embodiments of the present invention provide densitometers. An exemplary densitometer 210 is schematically depicted in FIG. 3. Densitometer 210 includes an optical head 200 and a processor 205. Processor 205 may be implemented in software, hardware, or a combination thereof, according to embodiments of the invention. In one embodiment, processor 205 is a microprocessor. In one embodiment, processor 205 is a hardware circuit. The optical head 200 includes at least one illumination source 215 for illuminating an area and at least one sensor 220 for converting radiation received from the area to a signal. In one embodiment, the at least one illumination source 215 includes a light-emitting diode and the at least one sensor 220 includes a light-to-voltage (LTV) sensor. In some embodiments, a plurality of illumination sources are included in optical head 200, such as in one embodiment, an orange LED, a green LED, a blue LED, and a red LED. In one embodiment, the optical head 200 includes 4 LEDs and two light-to-voltage (LTV) sensors. The illumination sources and sensors are arranged to illuminate an area and receive radiation from the area, respectively as known in the art. The processor 205 is provided to convert the received radiation to a standardized signal indicative of standardized optical density, as described above. In some embodiments, the processor 205 is configured to compensate for the effects of heating of one or more of the illumination sources, as described above. In some embodiments, the densitometer 210 includes a memory coupled to the processor 205 storing a look-up table associating signals indicative of optical density with standardized signals indicative of standardized optical density, and/or for storing empirical C values for use in Equation (2) above during compensation for illumination source heating. In some embodiments, processor 205 is configured to perform pattern recognition during or after the densitometer takes a plurality of measurements. In embodiments including pattern recognition, the densitometer is configured to recognize a synchronization signal initiating a pattern.

Other electronics may be included in the densitometer 210 including, but not limited to, an analog-to-digital (A/D) converter, a digital-to-analog (D/A) converter, as known in the art. In some embodiments, an A/D converter is provided to read LED voltage. In some embodiments, the A/D converter further reads LTV voltages. In some embodiments, a D/A converter controls LED current. In one embodiment, a D/A converter and an A/D converter are provided on a printed circuit board along with the processor 205. A/D and D/A converters are well known in the art, and the particular converters used will depend on the type of illumination sources and sensors used, the speed desired, and the cost of the converter. In one embodiment, a 12 bit D/A converter is provided to control LED current, a 12 bit A/D converter is provided to read LED voltage, and a 16 bit A/D converter is provided to read LTV voltages. The converters in one embodiment are coupled to a processor with sufficient speed and memory to perform the above calculations. Components of the densitometer may generally be implemented as hardware, software, or a combination thereof.

Figure 4:
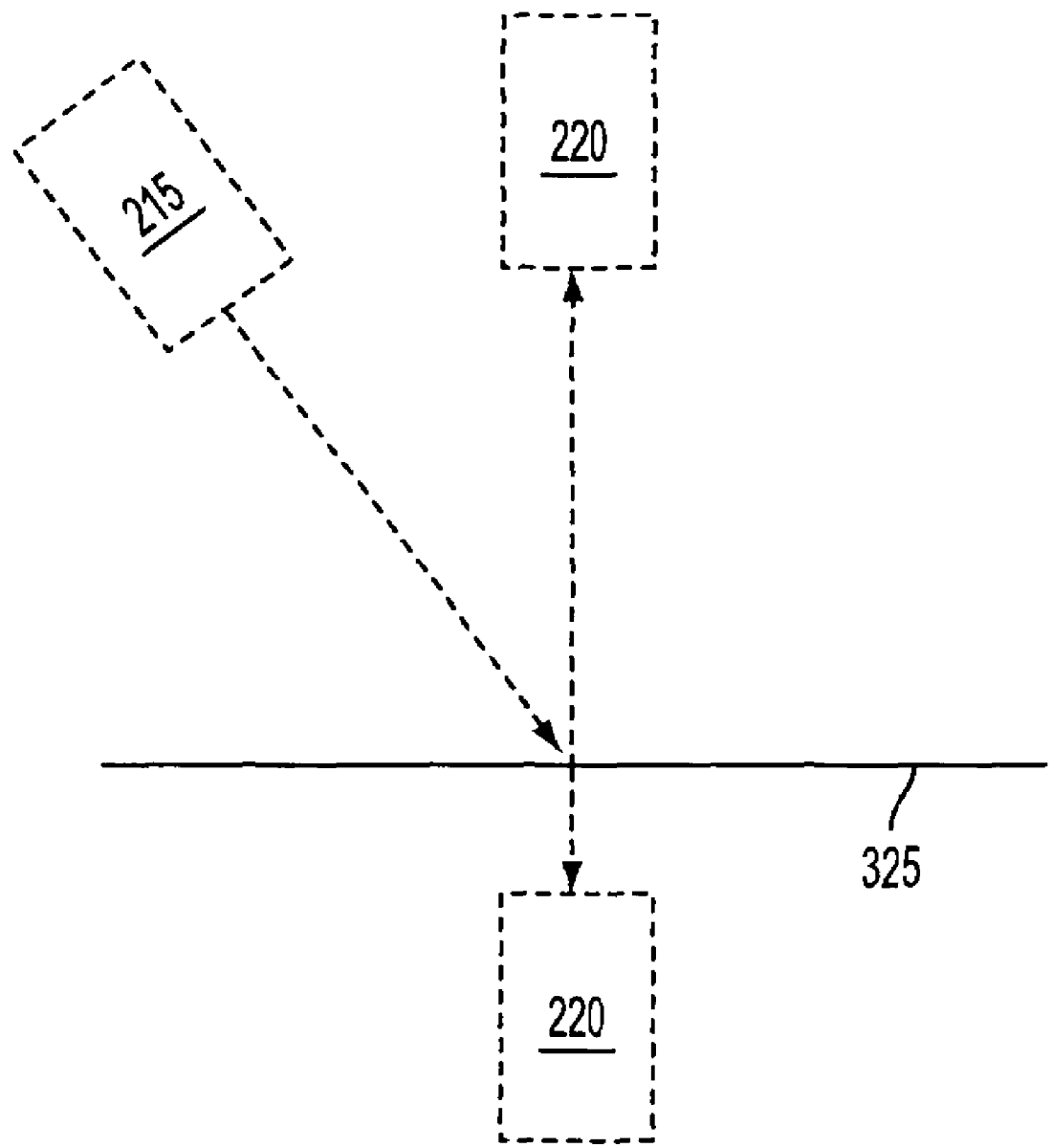
FIG. 4 depicts arrangements of an illumination source and a sensor according to embodiments of the present invention.

Components of the densitometer may be arranged in a variety of ways, according to embodiments of the invention. FIG. 4 depicts several arrangements of the illumination source 215 and the sensor 220 according to embodiments of the present invention. The present invention is not limited, however, to the configurations shown in FIG. 4. FIG. 4 depicts the placement of illumination source 215 and sensor 220 relative to printing media 325. Printing media 325 contains a printed area. The printing media 325 is any of a variety of media, in accordance with embodiments of the present invention, including but not limited to, paper, glossy paper, transparencies, fabric, metal, foil, plastics and polymers, skins or leather, glass, and the like. In some embodiments, sensor 220 receives radiation transmitted through the area. Accordingly, in those embodiments the illumination source 215 is placed on the opposite side of the printing media as the sensor 220, as shown in FIG. 4. In some embodiments, the illumination source 215 and the sensor 220 are positioned on the same side of printing media 325 and are arranged such that the sensor 220 receives radiation transmitted from the printing media 325. In some embodiments, one sensor in the densitometer is a specular sensor, allowing the densitometer to advantageously serve as a gloss meter.

Figure 5:
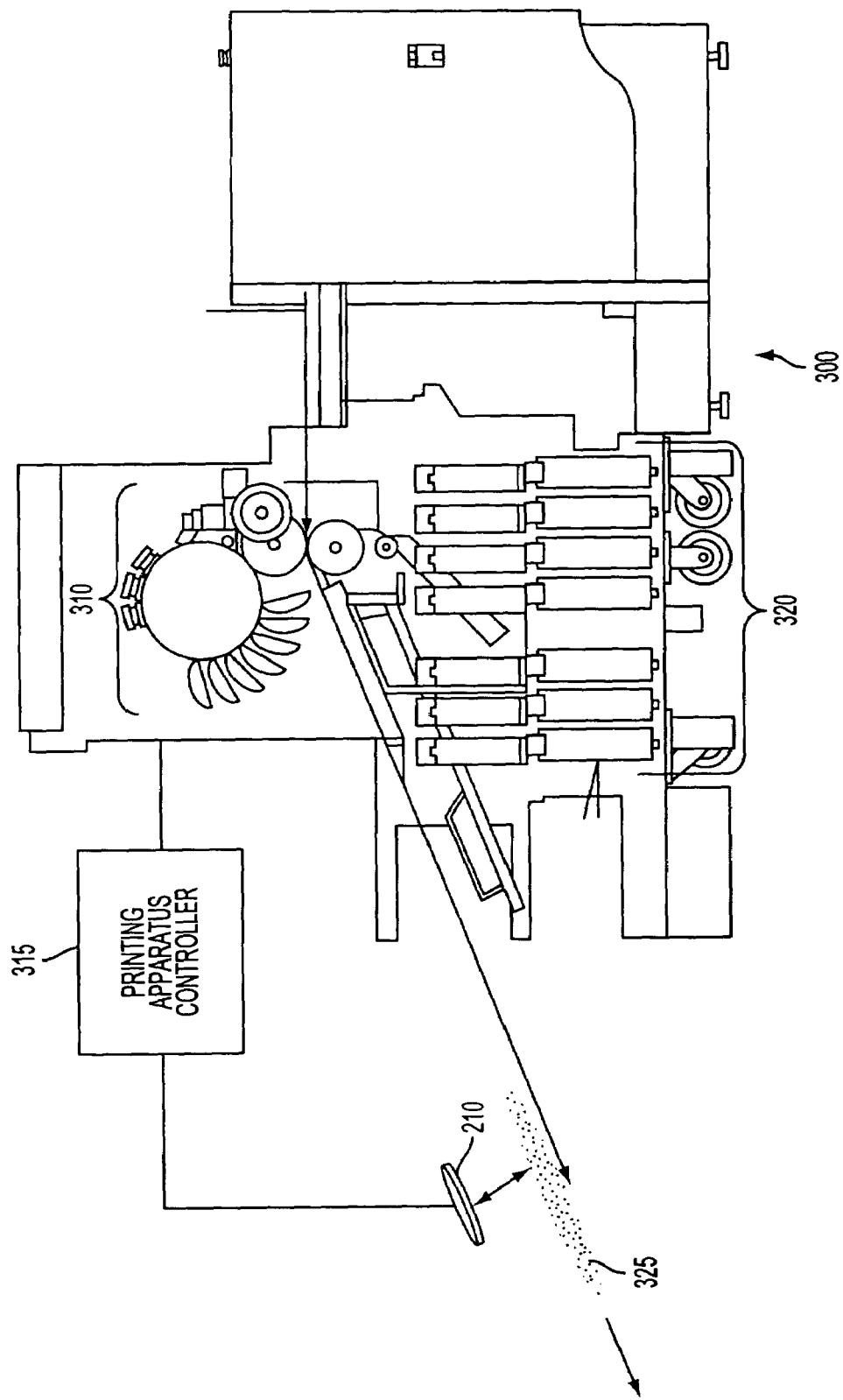
FIG. 5 depicts a printing apparatus, according to an embodiment of the present invention.

Embodiments of the present invention further provide a printing apparatus. An exemplary printing apparatus 300 is shown in FIG. 5. In some embodiments, the printing apparatus includes means for generating a signal indicating a color printed in an area, such as a printing apparatus controller 315. The printing apparatus 300 also includes means 310 to print one or more inks 320 on a printing media 325. In one embodiment, the means 310 includes a drum and one or more developers, as shown in FIG. 5 and known in the art for laser-driven printing in a digital printing press. However, other printing means may be used as means 310 including, but not limited to, inkjet printing mechanisms, bubble jet printing mechanisms, and other printing apparatus mechanisms as known in the art. As discussed above, any number of inks may be used including, but not limited to, 1, 2, 3, 4, 5, 6, 7, or more inks. The printing apparatus 300 further includes a densitometer 210 positioned to illuminate an area of the printing media 325 and receive radiation from the area. The densitometer 210 is coupled to the printing apparatus controller 315 and configured to determine the color being printed and generate a standardized signal indicative of standardized optical density of the area. The optical density measurements from the densitometer 210 are used to control ink thickness printed by means 310.

Embodiments of the present invention provide one or more documents or other articles printed with the printing apparatuses described above. Documents or other articles may include any of the printing media described above. Documents or other articles may include, but are not limited to, photographs, brochures, advertisements, literature, flyers, newspapers, magazines, compact discs (CDs) or other recording media, and the like. Other articles may also or alternatively be printed with the printing apparatuses described above. Documents or other articles may also be printed using the methods of measuring optical density described herein.

Methods and apparatuses according to embodiments of the present invention can be used in a variety of ways. Because the methods and densitometers according to embodiments of the present invention determine a color in an area, they select the appropriate illumination source, based on the color. Accordingly, optical density measurements taken according to embodiments of the present invention are faster than typical conventional measurements, where it is necessary to illuminate an area with a plurality of illumination sources, or illuminate through a plurality of filters, sequentially. In one embodiment, an optical density measurement takes less than 1 millisecond. In some embodiments, an optical density measurement takes less than 0.1 milliseconds. In some embodiments, an optical density measurement takes about 10 microseconds. In many embodiments a test strip having a plurality of test areas, each printed with a color is measured. In one embodiment, a 400 mm strip is read in 200 milliseconds while taking more than 1000 readings. Typical conventional devices and methods take hundreds of milliseconds for each such optical density measurement. Accurate heat compensation also improves the speed and accuracy of the measurement in some embodiments.

Embodiments of the present invention further provide increased resolution. In some embodiments, the resolution of area to be measured is less than 4 mm, in some embodiments less than 3.5 mm, in some embodiments less than 3 mm, in some embodiments less than 2.5 mm, in some embodiments less than 2 mm, in some embodiments the resolution is 1.6 mm, and in some embodiments it is less than this dimension or at intermediate dimensions. Other embodiments have larger than 4 mm resolution. In some embodiments with the specular sensor, the resolution achievable is 1.4 mm and larger.

Further, embodiments of the present invention allow a pattern (in one embodiment, a test strip) to be read at variable speed.

The foregoing descriptions of specific embodiments and best mode of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

We claim:

1. A method for measuring optical density, the method comprising:
   using electrical circuitry, determining a color on an area;
   using electrical circuitry, selecting, based on the color, one of a plurality of different illumination sources appropriate to determine optical density of the color on the area;
   illuminating the area with the selected illumination source;
   receiving radiation from the area responsive to the illuminating; and
   converting the received radiation to a signal indicative of optical density of the color on the area.

2. A method for measuring optical density according to claim 1, wherein the signal indicative of optical density comprises a standardized signal indicative of standardized optical density.

3. A method for measuring optical density according to claim 2, wherein the converting comprises:
   selecting a look-up table based on the color on the area, wherein the look-up table associates the received radiation with a standardized signal indicative of standardized optical density.

4. A method for measuring optical density according to claim 2, wherein the selected illumination source provides illumination having a first spectrum and said converting comprises compensating for at least one difference between the first spectrum and a standard spectrum to generate the standardized signal indicative of standardized optical density.

5. A method for measuring optical density according to claim 2, further comprising:
   generating a look-up table for converting the received radiation to the standardized signal indicative of standardized optical density.

6. A method for measuring optical density according to claim 1, wherein converting the received radiation to a signal indicative of optical density comprises:
   compensating for the effects of heating of the selected illumination source during illumination of the area.

7. A method for measuring optical density according to claim 6, wherein the selected illumination source comprises a light emitting diode and the compensating for the effects of heating comprises measuring the voltage across the light emitting diode.

8. A method for measuring optical density according to claim 7, wherein the compensating for the effects of heating further comprises generating a corrected signal indicative of optical density using a non-linear relationship between the voltage across the light emitting diode and the signal indicative of optical density.

9. An article printed using the method of measuring optical density of claim 1.

10. A method for measuring optical density according to claim 1, wherein the determining comprises using data regarding a marking agent used to print the color on the area.

11. A method for measuring optical density according to claim 10, wherein image data is used to print the color on the area, and wherein the data regarding the marking agent is accessed from the image data.

12. A method for measuring optical density according to claim 10, wherein the data is provided before the determining.

13. A method for measuring optical density according to claim 10, wherein the data is provided during the printing of the marking agent on the area and the data indicates the color of the marking agent used to print the color on the area.

14. A method for measuring optical density according to claim 10, further comprising accessing the data from storage circuitry.

15. A method for measuring optical density according to claim 1, wherein the determining comprises determining without sensing of the area.

16. A method for measuring optical density according to claim 1, wherein the determining comprises determining before completion of printing of the color on the area.

17. A method for measuring optical density according to claim 1, wherein the illuminating comprises illuminating only using the selected one of the different illumination sources, the receiving comprises receiving the radiation responsive to the illuminating using only the selected one of the different illumination sources, and the converting comprises converting only the received radiation to the signal indicative of the optical density of the color on the area.

18. A method for calibrating a printing apparatus, the method comprising:
   printing an area having a color;
   based on the color, automatically selecting one of a plurality of different illumination sources in a densitometer without user input;
   illuminating the area using the selected illumination source; and
   receiving a signal indicative of optical density in the area from the densitometer after the selecting.

19. A method for calibrating a printing apparatus according to claim 18, wherein:
   the printing comprises printing a plurality of areas, each having a color; and
   the receiving comprises receiving a signal indicative of optical density in each of the areas.

20. A method for calibrating a printing apparatus according to claim 18, wherein the signal indicative of optical density comprises a standardized signal indicative of standardized optical density.

21. A method for calibrating a printing apparatus according to claim 18, further comprising:
   compensating for the effects of heating of the selected illumination source during illumination of the area.

22. A method for calibrating a printing apparatus according to claim 18, wherein the printing comprises providing data regarding a color of a marking agent used for the printing, and wherein the automatically selecting comprises selecting using the data.

23. A method for calibrating a printing apparatus according to claim 18, wherein the illuminating comprises illuminating only using the selected one of the different illumination sources, and further comprising generating the signal indicative of the optical density in the area using only the illuminating of the area using only the selected one of the different illumination sources.

24. A densitometer comprising:
   a plurality of illumination sources to illuminate an area;
   a sensor for converting radiation received from the area; and
   a processor coupled to the sensor for converting the received radiation to a standardized signal indicative of standardized optical density; and
   wherein the processor is further configured to determine a color of the area and select one of the different illumination sources for use to determine the standardized optical density of the color of the area, and wherein the selection is responsive to the determination of the color.

25. A densitometer according to claim 24, wherein the plurality of illumination sources comprise light emitting diodes.

26. A densitometer according to claim 24, wherein the processor is further configured to compensate for the effects of heating of the illumination sources during illumination.

27. A densitometer according to claim 24, wherein the processor is configured to select the one illumination source using data generated during printing of a marking agent on the area.

28. A densitometer according to claim 24, further comprising a memory coupled to the processor, wherein the memory stores a look-up table for converting the received radiation to the standardized signal indicative of standardized optical density.

29. A densitometer according to claim 24, wherein the illumination sources are selected from the set consisting of red, green, blue, and orange.

30. A densitometer according to claim 29, wherein the selected one of different illumination sources is selected from the plurality of illumination sources based on the selected one of the different illumination sources having a color that is substantially a color complement to an area of a media to be measured.

31. A densitometer according to claim 24, further comprising a memory for receiving and storing data regarding inks used to print one or more areas to be measured, and means for accessing the stored data to determine the color printed on an area, the data being used to select a spectral wavelength of the selected one of the different illumination sources.

32. A densitometer according to claim 24, wherein the selected one of the different illumination sources is exactly a single illumination source having a spectral wavelength range narrower than the spectrum of visible white light.

33. A densitometer according to claim 32, wherein the selected one of the different illumination sources having a spectral wavelength range narrower than the spectrum of visible white light comprises a light emitting diode having one of a red, green, blue, or orange color spectral output.

34. A densitometer according to claim 24, wherein the standardized optical density provides optical density information in accordance with a standard predefined before the conversion of the received radiation to the standardized signal.

35. A densitometer according to claim 34, wherein the processor is configured to convert the received radiation to a signal indicative of optical density and to convert the signal indicative of optical density to the standardized signal indicative of standardized optical density.

36. A printing apparatus comprising:
   means for printing at least one ink on an area;
   a controller coupled to the means for printing; and
   a densitometer coupled to the controller, the densitometer positioned to illuminate the area and generate a standardized signal indicative of standardized optical density of the area responsive to the illumintion; and
   wherein the densitometer is configured to determine the color of ink printed on the area and to select at least one of a plurality of different illumination sources for the illumination and corresponding to the determination of the color of ink.

37. The printing apparatus of claim 36, wherein the densitometer comprises at least one light emitting diode.

38. The printing apparatus of claim 36, wherein the densitometer comprises a sensor positioned to receive radiation from the area.

39. A printing media printed with the printing apparatus of claim 36.

40. The printing apparatus of claim 36, wherein the means for printing comprises means for providing data regarding the at least one ink, and the selected at least one of the different illumination sources of the densitometer is selected for the illumination using the data regarding the at least one ink.

41. The printing apparatus of claim 40, wherein the data is provided before completion of the printing of the at least one ink on the area.

42. The printing apparatus of claim 36, wherein the standardized optical density provides optical density information according to a standard predefined before the illumination of the area.

43. The printing apparatus of claim 42, wherein the densitometer is configured to convert a signal indicative of optical density to the standardized signal indicative of standardized optical density.

* * * * *

UNITED STATES PATENT AND TRADEMARK OFFICE
CERTIFICATE OF CORRECTION

PATENT NO.         : 7,502,116 B2                                    Page 1 of 1
APPLICATION NO.    : 10/658939
DATED              : March 10, 2009
INVENTOR(S)        : Omer Gila et al.

It is certified that error appears in the above-identified patent and that said Letters Patent is hereby corrected as shown below:

In column 10, line 45, in Claim 33, delete "or" before "orange".

In column 10, line 62, in Claim 36, delete "illumintion" and insert -- illumination --, therefor.

In column 11, line 12, in Claim 40, delete "illumination" and insert -- illuminant --, therefor.

Signed and Sealed this

Sixth Day of October, 2009

David J. Kappos
*Director of the United States Patent and Trademark Office*